US008748087B2

(12) United States Patent
Wen et al.

(10) Patent No.: US 8,748,087 B2
(45) Date of Patent: Jun. 10, 2014

(54) SEQUENCE OF REVERSE TRANSCRIPTASE GENE AND METHOD OF USE

(75) Inventors: Yu-Mei Wen, Shanghai (CN); Yong-Xiang Wang, Shanghai (CN); Zhang-Mei Ma, Shanghai (CN)

(73) Assignee: Fudan University, Shanghai (CN)

( * ) Notice: Subject to any disclaimer, the term of this patent is extended or adjusted under 35 U.S.C. 154(b) by 1269 days.

(21) Appl. No.: 11/614,062

(22) Filed: Dec. 20, 2006

(65) Prior Publication Data
US 2007/0154490 A1 Jul. 5, 2007

(30) Foreign Application Priority Data
Dec. 29, 2005 (CN) .......................... 2005 1 0112431

(51) Int. Cl.

| | |
|---|---|
| *C12Q 1/70* | (2006.01) |
| *C12Q 1/68* | (2006.01) |
| *C12Q 1/18* | (2006.01) |
| *A61K 49/00* | (2006.01) |

(52) U.S. Cl.

USPC .................. 435/5; 435/6.13; 435/32; 424/9.2

(58) Field of Classification Search
None
See application file for complete search history.

(56) References Cited

U.S. PATENT DOCUMENTS

2002/0133297 A1* 9/2002 Yang et al. ...................... 702/19

OTHER PUBLICATIONS

Lin, X. et al. "A Single Amino Acid in the Reverse Transcriptase Domain of Hepatitis B Virus Affects Virus Replication Efficiency"Journal of Virology, 75(23):11827-11833, 2001.*
Wang, M. et al. "Non-nucleoside Analogue Inhibitors Bind to an Allosteric Site on HCV NS5B Polymerase. Crystal Structures and Mechanism of Inhibition" J. Biol. Chem., Mar. 2003; 278: 9489-9495.*
Deres K, et al. "Development of resistance and perspectives for future therapies against hepatitis B infections: lessons to be learned from HIV". Infection. 1999; 27 Suppl 2:S45-51.*
GenBank: AF100309.1 Hepatitis B virus strain 56, complete genome, Mar. 1999. p. 1-3.*
Le Guerhier F et al. Characterization of the antiviral effect of 2',3'-dideoxy-2', 3'-didehydro-beta-L-5-fluorocytidine in the duck hepatitis B virus infection model. Antimicrob Agents Chemother. Jan. 2000;44(1):111-22.*
Wang M et al. Non-nucleoside analogue inhibitors bind to an allosteric site on HCV NS5B polymerase. Crystal structures and mechanism of inhibition. J Biol Chem. Mar. 14, 2003;278(11):9489-95. Epub Dec. 30, 2002.*
Chouteau P et al. Inhibition of hepatitis B virus production associated with high levels of intracellular viral DNA intermediates in iron-depleted HepG2.2.15 cells. J Hepatol. Jan. 2001;34(1):108-13.*

* cited by examiner

*Primary Examiner* — Mary E Mosher
*Assistant Examiner* — Nick Zou
(74) *Attorney, Agent, or Firm* — Yuan Qing Jiang (57) ABSTRACT

The present invention provides an isolated polynucleotide acid comprising a polynucleotide sequence having a substantial amount of sequence identity to the entire length of the polynucleotide sequence as set forth in SEQ ID NO: 1 or its complementary strand (SEQ ID NO: 2), the sequence is derived from RT domain of HBV polymerase gene. The present invention also provides a polypeptide and related compositions, as well as methods for using the same.

14 Claims, 6 Drawing Sheets

SEQUENCE OF REVERSE TRANSCRIPTASE GENE AND METHOD OF USE

CROSS-REFERENCE TO RELATED APPLICATION

This application claims the benefit of Chinese Patent Application Ser. No. 200510112431.8 filed on Dec. 29, 2005, the entire content of which is hereby incorporated by reference in this application.

FIELD OF INVENTION

This invention relates to isolated nucleic acid and amino acid sequences of Hepatitis B Virus and methods of using the same.

BACKGROUND OF INVENTION

Hepatitis B virus (HBV) is a member of the Hepadnaviridae family and is a major pathogen causing acute and chronic viral hepatitis in human. Two billion people have been infected worldwide, of which more than 350 million have chronic HBV infections (WHO statistics data). HBV infection is endemic in certain areas in Asia. The prognosis of viral hepatitis B is especially poor in patients who were infected perinatally and suffered from chronic viral hepatitis B with replicative HBV infection, wherein usually serum Hepatitis B e Antigen (HBeAg) is persistently present. Over the years the patients have high probability to develop complications such as liver cirrhosis and hepatocellular carcinoma.

Hepatitis B is transmitted via body fluids containing the virus. The most common routes of HBV transmission are blood or other blood products transfusions, re-use of contaminated needles, unprotected sexual contact, and vertical transmission from mother to infant during childbirth. Ninety percent of infants infected may develop chronic HBV infection later in life.

Prevention is the primary way to stop HBV transmission among population at present. Safe and effective recombinant vaccines are available for prevention of HBV infection, and vaccination programs for general public are common practice in many countries now.

No effective way to cure chronic HBV infection has been established. The US Food and Drug Administration (FDA) has approved five drugs (lamivudine, entecavir, adefovir dipivoxil, interferon alfa-2b and pegylated interferon alfa-2a,) for the treatment of patients with chronic hepatitis B. The drugs are known to inhibit the replication of HBV and thus can slow down the course of the disease and the development of complications. However, less than 30% overall response rates and dose-dependent side effects restricted the use of interferon alpha. On the other hand, prolonged use of lamivudine, entecavir and adefovir dipivoxil to emergence of drug resistant HBV mutants also limited its use for long term therapy of chronic hepatitis B patients. Post-exposure prophylaxis with hepatitis B immune globulin is also known effective to prevent non-immune individuals from the infection after an exposure such as a needle stick. Yet chronic hepatitis patients face uphill battle to achieve their HBV virus free state, and new anti-HBV target which may substitute or complement the above mentioned drugs leading to cure HBV infection still awaits for the development of medical research.

SUMMARY OF THE INVENTION

The present invention fulfills the needs of curing HBV infection by providing a novel polynucleotide, polypeptide and related compositions as anti HBV targets, as well as methods of using the same.

In particular and by way of example only, provided is an isolated polynucleotide acid comprising a polynucleotide sequence having a substantial amount of sequence identity to the entire length of the polynucleotide sequence as set forth in SEQ ID NO: 1 or SEQ ID NO: 2, said sequence is derived from RT domain of HBV polymerase gene.

Within another aspect of the present invention, provided is an isolated polypeptide comprising an amino acid sequence having a substantial amount of sequence identity to the entire length of the amino acid sequence as set forth in SEQ ID NO: 3, wherein said amino acid sequence is capable of positioning a template on RT300-311 in RT domain of HBV polymerase to perform reverse transcription.

In yet another embodiment, provided is a polypeptide comprising a recombinantly-produced or chemically-synthesized amino acid sequence comprising a substantial amount of sequence identity to the entire length of the amino acid sequence as set forth in SEQ ID NO: 3.

Within a further aspect of the present invention, provided is a method of inhibition of HBV replication comprising administering a patient with a drug comprising a recombinant vector comprising a polynucleotide acid as set forth in SEQ ID NO: 1 or SEQ ID NO: 2, said polynucleotide sequence inhibit HBV pgRNA encapsidation, thereby stopping the HBV replication process.

Within an additional aspect of the invention there is provided a method for screening inhibitors to bind the polynucleotide comprising the steps: 1) providing a polynucleotide acid as an anti HBV target having a substantial amount of sequence identity to the entire length of the polynucleotide sequence as set forth in SEQ ID NO: 1 or SEQ ID NO: 2, said sequence is derived from RT domain of HBV polymerase gene, 2) providing a candidate substance from a population of substances, 3) introducing the candidate substance to react with the polynucleotide acid, and 4) detecting the effect of inhibition of HBV replication.

Within a further aspect of the invention there is provided a method for screening inhibitors to bind the polypeptide comprising the steps: 1) providing an amino acid sequence of the polypeptide as an anti HBV target having a substantial amount of sequence identity to the entire length of the polypeptide sequence as set forth in SEQ ID NO: 3 derived from RT domain of HBV polymerase, 2) providing a candidate substance from a population of substances, 3) introducing the candidate substance to react with the polypeptide, and 4) detecting the effect of inhibition of HBV replication.

These and other aspects of the invention will become evident upon reference to the following detailed description and the attached drawings.

DETAILED DESCRIPTION OF THE INVENTION

HBV has unique genetic and biological characteristics. The virus has a genome of circular double-strand DNA with a single-stranded gap. The length of the negative strand DNA is approximately 3.2 kb, and its plus strand DNA is approximately 50-100% of the length of the minus chain.

To date, eight genotypes A, B, C, D, E, F, G, H of HBV strains (HBV genotype A-H) are reported, and certain genotypes are shown to be associated with poor prognosis of HBV infection.

In general, HBV genome consists of four open reading frames (genes), which are envelope gene (Pre-S/S), core gene (Pre-C/C), X gene (X), and polymerase gene (P). Envelope gene encodes envelope protein, core gene encodes pre-core/core protein, X gene encodes transactivating X protein, and polymerase gene encodes viral polymerase.

During HBV replication, each of the protein produced from HBV genome serves its unique function. The pre-core protein is later processed to be viral e antigen (HBeAg). The function of protein X is not yet clear, it may be involved in the activation of host cell genes and the development of cancer. The P gene expends approximately three fourth of the entire coding region and overlaps with each of the three other genes, its protein product, polymerase, performs multiple functions during HBV life cycle.

HBV life cycle starts with HBV virion entering hepatocyte via receptor-mediated uptake. The virion uncoats and its capsid is transported into the nucleus of the hepatocyte, where the capsid disassembles, releasing the open circular viral genome. A covalently closed circular DNA (cccDNA) is formed in the nucleus, which serves as a transcriptional template of the virus.

HBV replicates through an RNA intermediate named pregenomic RNA (pgRNA), and relies on reverse transcription process. For a non-retroviral DNA virus like HBV, reverse transcription is part of its unique replication process, since reverse transcription is usually characteristic of RNA viruses such as retroviruses. Typically, a retrovirus uses reverse transcription to transcribe its genomic RNA to DNA, and then incorporates the DNA into the genome of the host cell, example of which is the replication process of Human Immunodeficiency virus (HIV), a retrovirus that causes Acquired Immune Deficiency Syndrome (AIDS). The difference between HBV's reverse transcription process and retroviral reverse transcription process is that HBV reverse transcribes pgRNA into viral DNA in a newly synthesized viral particles (capsids) at the late stage of its replication, whereas retroviral RNA virus reverse transcribes viral RNA into DNA to incorporate in the genome of the host cell, at the early stage of its replication.

Once the covalently closed circular DNA (cccDNA) of HBV is in the host cell nucleus, the HBV replication continues with transcription of viral mRNAs (pgRNA, preC mRNA, preS/S mRNA and X mRNA). The preC mRNA encodes the precursor of e antigen and pgRNA encodes core protein and polymerase.

HBV polymerase together with core proteins, pgRNA and host factors assemble to core particles (capsids) of the virus. In the capsids the HBV double strand DNA is replicated. The intermediate pgRNA is reverse transcribed to HBV minus strand DNA, catalyzed by the polymerase, and the minus strand DNA is then used as a template to replicate the entire HBV genome.

Some of the capsids move to the ER membrane and then to Golgi complex, coated with the envelope proteins, and bud out of the hepatocyte, acquiring their coating along their secreting way of exit. The rest of the capsids move back to the nucleus, disassemble and release their HBV DNA to expand the pool of cccDNA and repeat the HBV replication process.

HBV polymerase plays multiple roles in HBV life cycle and is vital to HBV replication. HBV polymerase encoded by P gene of HBV genome can be further divided into four domains, according to mutational analysis and sequence alignment of HBV polymerase with retroviral reverse transcriptase (RT) counterparts. One of the four domains is terminal protein (TP), which is unique to HBV and is a protein primer. The second domain is a spacer region, which is dispensable for polymerase activity. The third domain is reverse transcriptase (RT) domain, which bears a tyrosine-methionine-aspartic acid-aspartic acid (YMDD) motif to catalyze RNA and DNA dependent DNA polymerization. The fourth domain is RNaseH domain, which degrades the RNA strand of RNA-DNA hybrids produced during HBV reverse transcription.

The detailed function of polymerase in HBV reverse transcription is further described in the following paragraphs. TP domain acts as a protein primer to initiate reverse transcription using the stem-loop structure close to the 5' end of pgRNA as a template. The progeny viral DNA synthesis is accomplished by alternatively utilizing RNA dependent DNA polymerase, RNaseH and DNA dependent DNA polymerase activities, all of which are the activity of HBV polymerase. Furthermore, HBV polymerase, which acts as a necessary component together with pgRNA, core proteins and other cellular factors such as Hsp90 and p23, participates in encapsidation and assembly of capsids.

To better understand its role in reverse transcription, the three dimensional structure model of HBV polymerase is analyzed and shown as a topology shape of a right-hand with several subdomains. This right-hand shape is a common feature of the three dimensional structure of many polymerases, disregarding the variation of the amino acid sequence, and the eight HBV genotypes from which the polymerase is originated. The right-hand shape structure may also be a shared feature of many polymerases cross-species, suggesting some important enzymatic function of polymerase is related to the feature, and further studies are warranted to identify each subdomain of the polymerase.

Different subdomains of polymerase fulfill different functions. Crystallographic study has revealed that the structure of each of the polynucleotide polymerase comprises the "thumb", the "palm" and the "fingers" subdomains as their common features. The palm subdomain harbors the catalytic center for the nucleotidyl transfer reaction, while the fingers subdomain interacts with the nucleoside triphosphate and with the template. The function of thumb subdomain is to position the template correctly, and to execute translocation of polymerase on the template.

Based on secondary structure alignment and crystallographic data analysis, a helix-turn-helix named "helix clamp", which is a special part of secondary structure located at the thumb subdomain of the polymerase is found common to all kinds of polynucleotide polymerase. Further experiments of mutational analysis and molecular modeling on helix clamps of HIV reverse transcriptase and of Klenow fragment (a 68-kDa carboxyl-terminal fragment of *Escherichia coli* DNA polymerase I) indicate that the two helix clamps bind the nucleic acid template and primer individually during polymerization reaction. Mutation experiments on the two helix clamps show that the mutated polymerases have reduced enzyme activity.

Crystallographic data from the complex of Hepatitis C Virus (HCV) RdRp and inhibitors (phenylalanine derivatives, cyclopentyl dihydropyran-2-ones, Indole-derivatives, thiophene 2-carboxylic acid and its derivatives) showed that some helix-turn-helix residues are involved in the binding of inhibitors to RdRp. (J. Biol. Chem., 2003, 278: 9489-95, Journal of Virology, 2003, 77: 7575-81, J. Biol. Chem., 2005, 280: 29765-70, J. Biol. Chem., 2005, 280: 18202-10). The term "helix-turn-helix" used herein, refers to a major protein structural motif capable of binding DNA. It is composed of two α helices joined by a short strand of amino acids named "turn" and is found in many enzymes that regulate gene expression. The helix-turn-helix motif facilitates DNA recognition. In particular, recognition and binding to DNA is done by the two α helices, one occupying the N-terminal end of the motif, the other at the C-terminus. In most cases, the second helix contributes most to DNA recognition, and hence it is often called the "recognition helix". It binds to the major groove of DNA through a series of hydrogen bonds and various Van der Waals interactions with exposed bases. The other α helix stabilizes the interaction between protein and DNA, but does not play a particularly strong role in its recognition. Furthermore, the helix-turn-helix residues are conserved in the HBV reverse transcriptase (HBV RT) and the binding site of the inhibitors is located at the base of the thumb subdomain, so it is anticipated that these inhibitors would also inhibit HBV polymerase by antiviral assay known to the skilled person on HBV producing stable cell line such as HepG2.2.15 cell line and HepAD38 cell line. Since helix-turn-helix (helix clamp) of HBV RT plays important roles in HBV replication and encapsidation, helix-turn-helix can be used as a new anti-HBV target for anti-HBV agent design.

Currently, most research works are focused on "palm" subdomain of the right-hand shape of polymerase. The six functional regions of reverse transcriptase (RT) of polmerase are mapped. They are located on the RT's amino acid sequence residues 37-47, 75-91, 163-189, 200-210, 230-241, 247-257, and are arranged as F, A, B, C, D and E regions from N terminal of the sequence. However, up till now there is neither report indicating whether the "thumb" subdomain of HBV reverse transcriptase (HBV RT) is functional, nor research evidence indicating whether the helix-turn-helix (helix clamp) of HBV RT is functional in the replication of HBV.

Based on above description, the helix-turn-helix (helix clamp) of HBV RT is involved in HBV pgRNA encapsidation. In vitro synthesized peptides antagonizing or mimicking the helix-turn-helix or covering part of, or even the complete sequence of the "helix clamp" can be used to interfere with the virus encapsidation.

Figure 1:
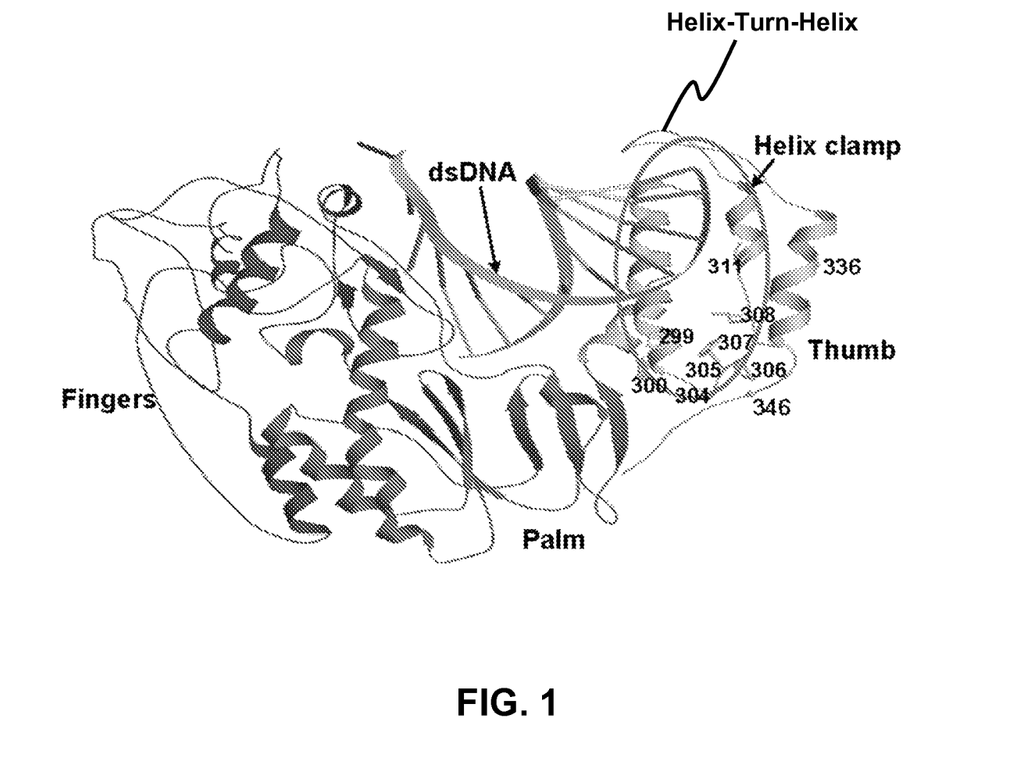
FIG. 1 shows a ribbon diagram of the helix clamp at three-dimensional model of the RT domain of HBV polymerase.

Amino acid sequence residues RT 300-311 region in the thumb subdomain of HBV reverse transcriptase (HBV RT) is found highly conserved among all eight HBV genotypes. The consensus amino acid sequence of residues RT300-311 in the thumb subdomain is FTQCGYPALMPL (SEQ ID NO: 3, Phe Thr Gln Cys Gly Tyr Pro Ala Leu Met Pro Leu, from N terminal to C terminal, RT300-RT311 at RT domain of HBV polymerase), based on experiment results of amino acid sequence alignment. In accordance with one embodiment of the present invention, amino acid sequence as set forth in SEQ ID NO: 3 is capable of positioning a template on RT300 to RT311 in RT domain of HBV polymerase to perform reverse transcription. The amino acid residues in RT300-311 region are located at the helix-turn-helix (helix clamp) of HBV RT. FIG. 1 shows a ribbon diagram of the helix clamp at three-dimensional model of the RT domain of HBV polymerase (residues 325 to 699). Helix clamp region and residues RT304 to RT346 are labeled on the figure, wherein the helix-turn-helix is also indicated on the figure. The figure also shows the binding of a double-stranded DNA (dsDNA) part of the model, and palm, fingers, and thumb subdomains of the model.

Figure 2:
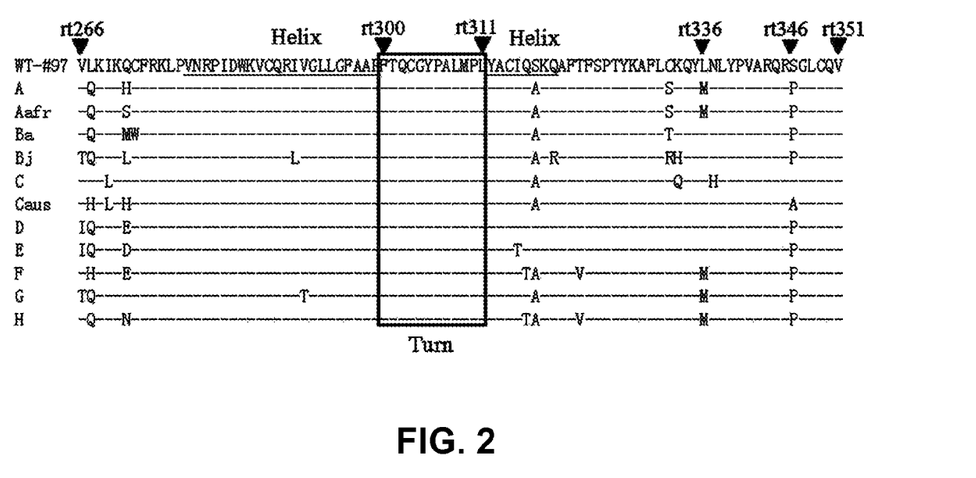
FIG. 2 shows sequence alignment of the thumb subdomains, wherein SEQ ID NO: 3 is shown from rt300 to rt311.

FIG. 2 shows sequence alignment of the thumb subdomains of A-X02763, Aafr-AF297621, Ba-D00330, Bj-AB073858, C-AB033556, Caus-AB048704, D-X02496, E-X75657, F-X69798, G-AF160501 and H-AY090454 (A, B, C, D, E, F, G and H) genotypes of HBV RT compared with wild type HBV WT-#97. The comparison shows residues RT300 to RT311 (SEQ ID NO: 3) are conserved and some other residues, such as RT336 are also conserved.

Figure 3:
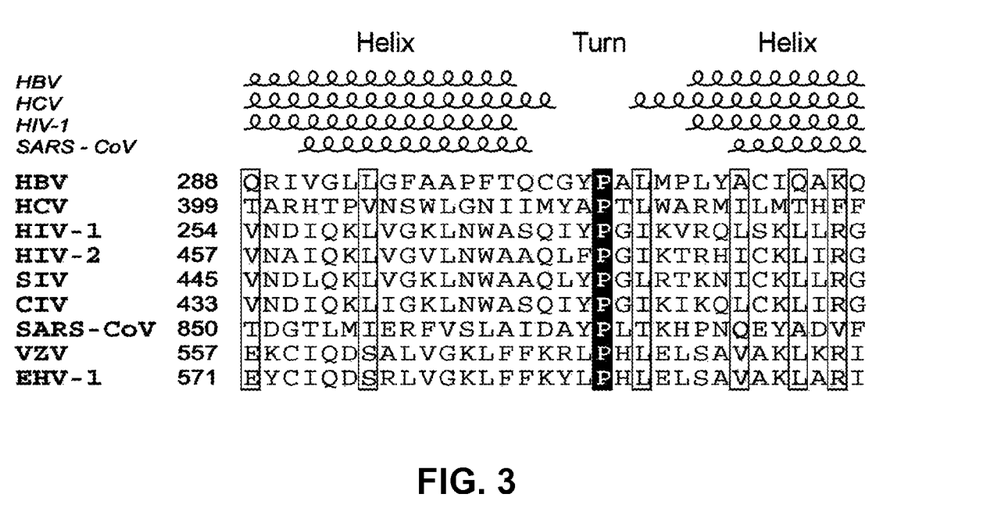
FIG. 3 shows sequence alignment of the helix-turn-helix (helix clamp) of HBV polymerase with similar structure of representatives from three classes of viruses. The sequences are displayed from the top line toward the bottom line of FIG. 3: The top line of sequence is HBV sequence, showing SEQ ID NO: 3 starting from amino acid groups rt300 to rt311 (SEQ ID NO: 3 rt300 to rt311 is within the part of the SEQ ID NO: 5, which is the whole top line sequence.), and SEQ ID NO: 5 (the entire top line sequence) from amino acid groups rt288 to rt319. The second line of sequence is HCV sequence, showing SEQ ID NO: 6 from amino acid groups rt399 to rt430. The third line of sequence is HIV-1 sequence, showing SEQ ID NO: 7 from amino acid groups rt254 to rt285. The 4th line of sequence is HIV-2 sequence, showing SEQ ID NO: 8 from amino acid groups rt457 to rt488. The 5th line of sequence is SIV sequence, showing SEQ ID NO: 9 from amino acid groups rt445 to rt476. The 6th line of sequence is CIV sequence, showing SEQ ID NO: 10 from amino acid groups rt433 to rt464. The 7th line of sequence is SARS-CoV sequence, showing SEQ ID NO: 11 from amino acid groups rt850 to rt881. The 8th line of sequence is VZV sequence, showing SEQ ID NO: 12 from amino acid groups rt557 to rt588. The 9th line of sequence is EHV-1 sequence, showing SEQ ID NO: 13 from amino acid groups rt571 to rt602.

FIG. 3 shows sequence alignment of the helix-turn-helix (helix clamp) of HBV polymerase with similar structure of representatives from three classes of viruses: RNA virus (HCV, SARS-CoV), retrovirus (HIV, SIV and CIV) and DNA virus (VZV, EHV-1). The result shows some of the residues are highly conserved. In the figure, the top line sequence depicts the turn of the helix-turn-helix of HBV, starting from residues rt300 to rt311 (SEQ ID NO: 3).

Figure 4:
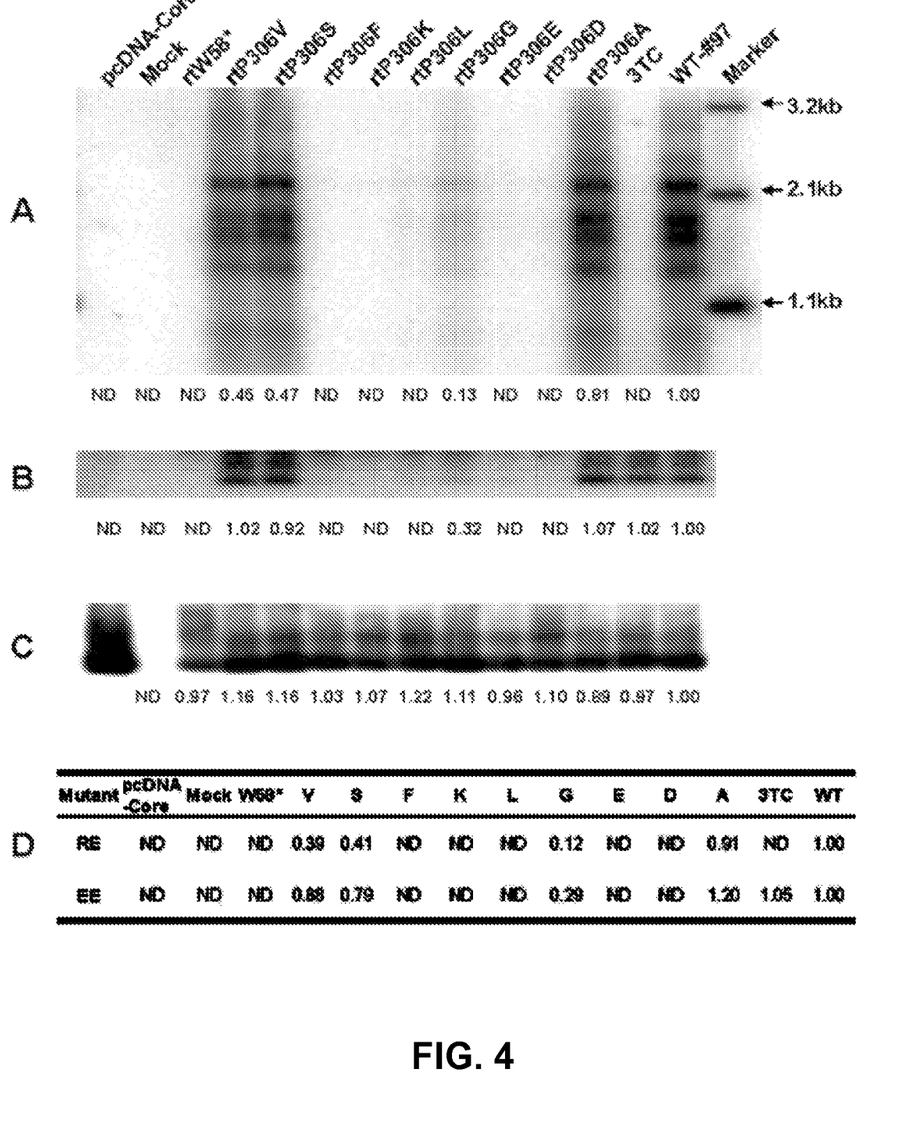
FIG. 4 shows decreased replication and encapsidation efficiencies of mutants substituted at RT306P with alanine or alternative amino acids.
Figure 5:
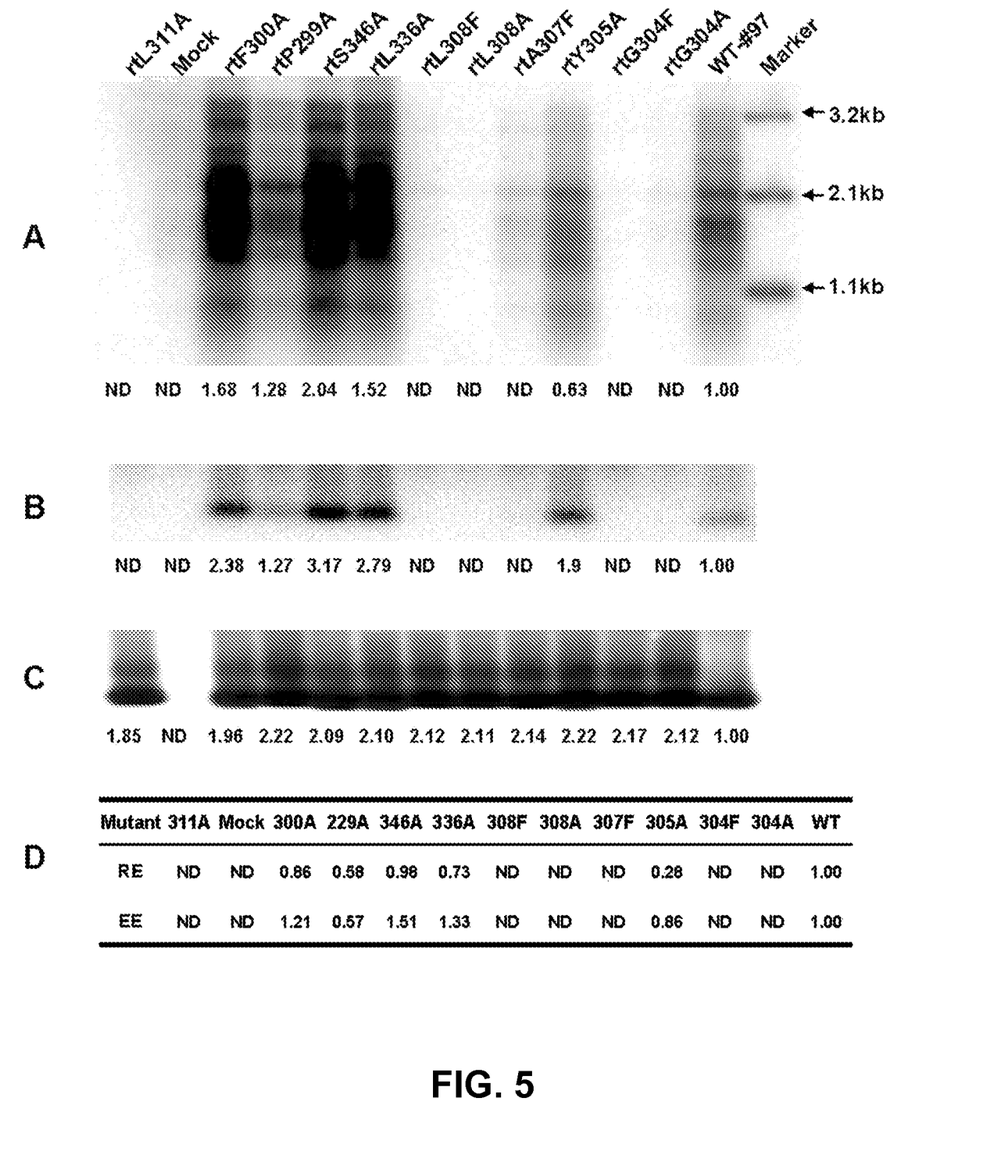
FIG. 5 shows decreased replication and encapsidation efficiencies of mutants substituted at helix-turn-helix residues other than RT306P with alanine or phenylalanine.

FIG. 4 and FIG. 5 show decreased replication and encapsidation efficiencies of mutants substituted at RT306P and other RT residues with alanine or alternative amino acids. Therefore, helix-turn-helix of HBV polymerase is vital to HBV replication.

Figure 6:
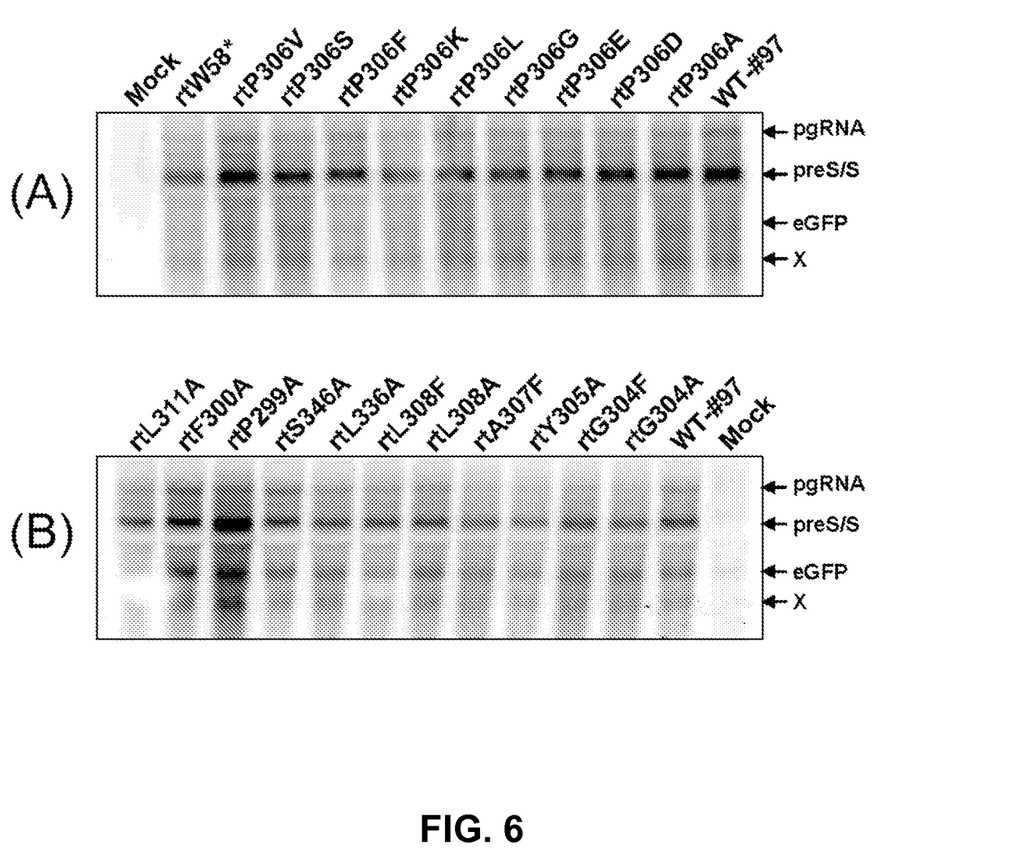
FIG. 6 shows that substitutions at helix-turn-helix residues did not interfere with HBV transcription.
Figure 7:
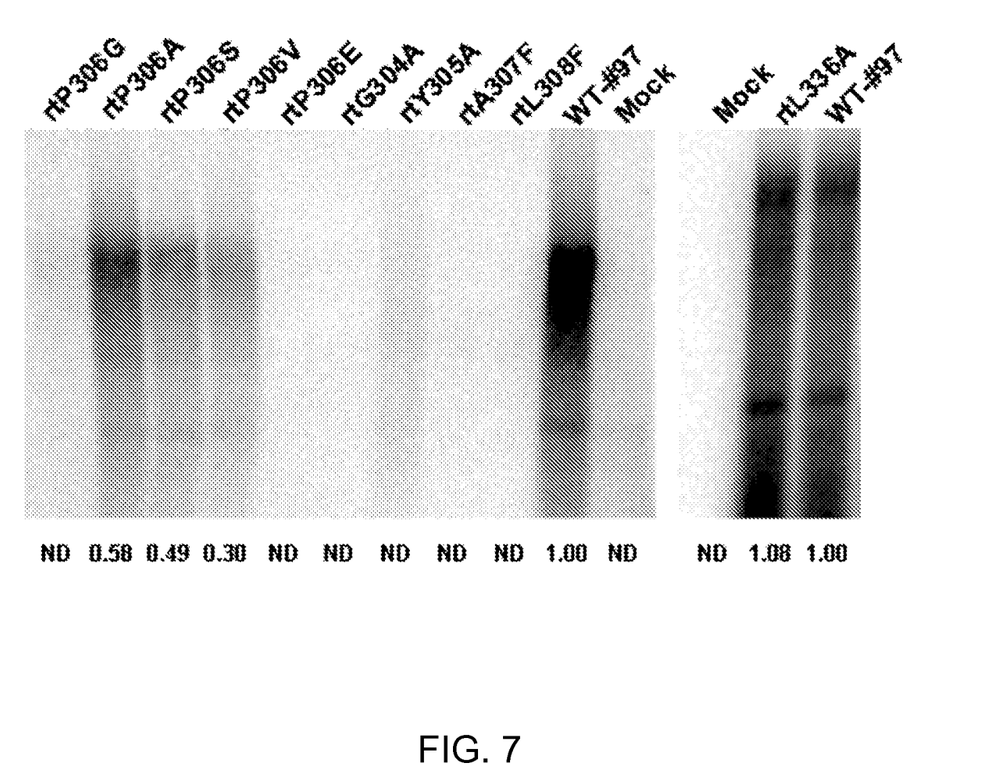
FIG. 7 shows some helix-turn-helix mutants with slightly changed pgRNA encapsidation and decreased polymerase activity.

FIG. 6 shows that substitutions at helix-turn-helix residues did not interfere with HBV transcription, and FIG. 7 shows that some helix-turn-helix mutants with slightly changed pgRNA encapsidation display decreased polymerase activity.

To explore the potential functions of the helix-turn-helix, a series of site directed helix-turn-helix mutants based on the context of 1.3 fold wild type HBV genome are constructed. The replication efficiencies and encapsidation efficiencies of the helix-turn-helix mutants are monitored by using cell transfection assay, Southern blotting results indicated that most of these mutants showed decreased replication efficiencies compared to the replication efficiencies of wild type strain, if the helix-turn-helix residues RT 306P, RT 304G, RT 305Y, RT 307A, RT 308L, and RT 311 L are changed to alanine or phenylalanine.

In accordance with one embodiment of the present invention, an isolated polynucleotide acid is identified. The isolated polynucleotide acid comprises a polynucleotide sequence having a substantial amount of sequence identity to the entire length of the polynucleotide sequence as set forth in SEQ ID NO: 1 (5'-TTTACACAATGTGGCTATCCTGCTTTAATGCCTTTA-3') or SEQ ID NO: 2 (5'-TAAAGGCATTAAAGCAGGATAGCCACATTGTGTAAA-3'), which is a complementary strand of SEQ ID NO: 1, said sequence is derived from RT domain of HBV polymerase gene.

According to Example One, a polynucleotide sequence as set forth in SEQ ID NO: 1 derived from RT domain of HBV polymerase gene was isolated, which is conserved in eight HBV genotypes, and its complementary sequence is SEQ ID NO: 2. As used herein, the language "isolated or recombinant polynucleotide sequence" includes a polynucleotide which is substantially free of cellular material or culture medium when produced by recombinant DNA techniques, or chemical precursors or other chemicals when chemically synthesized. In this invention, the polynucleotide sequence can be produced introducing the sequence into prokaryotic such as E. coli or eukaryotic host cells such as hepatocyte, Chinese hamster ovary cell or 293 cell, or yeast such as S. Cerevisiae with the aid of a recombinant vector or construct, operably linked to a promoter such as terminal protein (TP), T7, T3 or Sp6, using experiment procedures known to the person skilled in the arts such as transfection, transformation or electroporation. In addition to use an expression system mentioned above to prepare polynucleotide sequence, analogous polynucleotide sequence can also be prepared synthetically or prepared directly by isolation and purification from various HBV genotypes. The term "operably linked" means that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements.

A series of experiments, as described in Examples 2 through 9, were conducted. The experiments include plasmid constructs, point mutation on helix-turn helix residues RT 306P, RT 304G, RT 305Y, RT 307A, RT 308L, and RT 311L to alanine or phenylalanine, and other experiments such as cell culture and transfection, Isolation of intracellular replicative intermediates from transfected cells, Southern blotting, Northern blotting, HBV pgRNA packaging assay, Endogenous polymerase reaction (EPR), and Assay for inhibitory activity against HBV replication, to monitor the replication efficiencies and encapsidation efficiencies of the helix-turn-helix mutants.

The experimental results revealed that HBV polymerase activity is reduced, HBV pgRNA encapsidation efficiencies are decreased and HBV replication is hampered, if residues RT 300, RT 304, RT 305, RT 306, RT 307, RT 308 and RT 311 of HBV RT are mutated. The results proved that residues RT 300, RT 304, RT 305, RT 306, RT 307, RT 308 and RT 311 of HBV RT are highly conserved, and have the function of controlling HBV polymerase activity, influencing HBV pgRNA encapsidation efficiencies, and regulating HBV replication. The regulation of HBV replication is still effective if the isolated polynucleotide acid sequence varies substantial amount of the nucleotide sequence, which is at least 50% of the number of the nucleotides. The term "percent (%) identity" as used in the context of nucleotide sequence (e.g., when one nucleotide sequence is said to be X % identical to another nucleotide sequence) refers to the percentage of identical residues shared between the two sequences, when optimally aligned. To determine the percent identity of two nucleotide sequences, the sequences are aligned for optimal comparison purposes (e.g., gaps may be introduced in one sequence for optimal alignment with the other sequence). The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences. Based on the fact of the above mentioned function of polynucleotide of HBV RT, new drugs and biological substances can be designed and screened to act on the sequence, or interact with the sequence to interfere the replication of HBV replication. The new drugs and biological substances can be recombinant vector comprising at least one polynucleotide acid of SEQ ID NO: 1 or SEQ ID NO: 2, and antibodies targeting the amino acids derived from the polynucleotide acids, chemical compounds, polynucleotides, and herb medicines.

One embodiment of this invention is a method for screening inhibitors to bind the polynucleotide acid of SEQ ID NO: 1 or SEQ ID NO: 2, which is its complementary strand, base on the experiment samples. The term "inhibitor" when used herein, refers to recombinant vectors, antibodies, chemical compounds, polynucleotides, herb medicines, and any other molecules hamper the replication of HBV. The inhibitor screen comprises the steps of: 1) providing a polynucleotide acid as an anti-HBV target having a substantial amount of sequence identity to SEQ ID NO: 1 or SEQ ID NO: 2 derived from RT domain of HBV polymerase gene, 2) providing a candidate substance from a population of substances, 3) introducing the candidate substance to react with the polynucleotide acid, and 4) detecting the effect of inhibition of HBV replication. The candidate substances are antibodies, chemical compounds, polynucleotides, and herb medicines.

The method for screening inhibitors to bind the polynucleotide comprises building a candidate substance library from a population of substances, such as antibodies, chemical compounds, polynucleotides, and herb medicines, by predicting potential candidates by ligand orientation evaluation based on DOCK algorithm, steric complementarity, chemical complementarity, using the intermolecular van der Waals force, or the intermolecular electrostaticterms from the AMBER force-field.

The three dimensional model of HBV RT as a right-hand shaped secondary structure is analyzed. The results revealed that the helix-turn-helix of helix clamp, which is a special part of secondary structure of the polypeptide, is located at the base of the thumb subdomain of the polymerase of HBV RT. Furthermore, the helix clamp is found common to all of polynucleotide polymerases from eight genotypes A, B, C, D, E, F, G, H of HBV strains (HBV genotype A-H). The two helix clamps bind the nucleic acid template and primer individually during polymerization reaction. Small-molecule-sized "pockets" surrounding the helix-turn-helix of helix clamp is at the base of the thumb subdomain of the HBV RT polymerase, and can be located by using specific prediction methods such as DOCK algorithm. A list of molecules to bind to the "pockets" by ligand orientation evaluation based on certain criteria such as steric and chemical complementarity is generated. The mechanism that the molecules bind to the pockets and the common features of the molecules for screening experiments are:

1) The shape of the lead compound should match the pockets on the ligand.

2) Some groups of the compounds should form non-covalent binding bond or hydrogen bond with the molecules at the pockets.

The experiments to screen the anti-HBV agents, which are the inhibitors to HBV replication, are designed. The chemical compounds and other substances are screened and evaluated for their binding to the pockets of the helix-turn-helix residues in the HBV reverse transcriptase (HBV RT) located at the base of the thumb subdomain, using the intermolecular van der Waals and electrostaticterms from the AMBER forcefield. Non-covalent bond, such as intermolecular van der Waals force formed between the lead and ligand in the structure-based drug design, is a crucial criteria to select the promising lead from small molecule database, while the electrostaticterms from the AMBER force-field is to further evaluate the binding affinity of lead compound and the ligand. Other parameters of the substances such as solubility, toxicity and ease of analog synthesis, which are the prerequisite of a good lead and facilitate the efficacy detection using biological experiment procedures (cell culture, animal test and so on), are evaluated, and the substances are further screened and tested based on their inhibitory effects on the HBV replication in HBV producing stable cell line such as HepG2.2.15 cell line or HepAD38 cell line.

The database of small molecules for the screening experiments is available from commercial sources such as ACD v93.2, (Available Chemicals Directory, Molecular Design, San Leandro, Calif.), Naphthalenesulfonic acid and its derivatives (Bioorganic Chemistry 2002, 30: 443-58), Phenethylthiazolylthiourea (PETT) derivatives (Bioorg Med Chem Lett. 1998, 8: 2213-8), Dihydroalkoxybenzyloxopyrimidine (DABO) and its derivatives (Antimicrobial Agents and Chemotherapy 1998, 42: 3225-33), Thiourea compounds and their derivatives (Antiviral Chemistry & Chemotherapy 10: 233-240), Phenylalanine derivatives (J. Biol. Chem., 2003, 278: 9489-95), Cyclopentyl dihydropyran-2-ones (Journal of Virology, 2003, 77: 7575-81), Indole-derivatives (J. Biol. Chem., 2005, 280: 29765-70), Thiophene 2-carboxylic acid and its derivatives (J. Biol. Chem., 2005, 280: 18202-10), which are hereby incorporated as references. Additional data bases such as NCI DIS 3D Database (http://dtp.nci.nih.gov/docs/3d_database/dis3d.html), ComGenex, Inc. (Budapest, Hungary), ChemDB (http://cdb.ics.uci.edu/CHEM/Web/) providing other molecules which are suitable to above mentioned two screening criteria are also incorporated as references. The same databases can be also used for the anti HBV agent screening, in which an amino acid sequence as set forth in SEQ ID NO: 3 derived from the "thumb" subdomain of HBV RT is the target.

The method for screening inhibitors to bind the polynucleotide further evaluates the library of candidates for their solubility, toxicity, ease of analog synthesis, and the effect of inhibition of HBV replication. The inhibitory effects to HBV replication of the candidates are tested by reacting potential candidate substances with the polynucleotide acid having a substantial amount of sequence identity to SEQ ID NO: 1 or SEQ ID NO: 2 derived from RT domain of HBV polymerase gene in assays, in animal models, and with patients clinically for their inhibitory activity against HBV replication. In addition, toxilogical data of potential candidate substances are collected using animal models.

One embodiment of this invention is a method for screening inhibitors to bind the helix-turn-helix of the helix clamp of RT domain of HBV polymerase (FIG. 1). Base on the experiment samples again, an amino acid sequence as set forth in SEQ ID NO: 3 derived from the "thumb" subdomain of HBV RT (FIG. 1) is isolated, which is conserved in eight HBV genotypes. The term "isolated or recombinant polypeptide", when used herein, encompasses of chains of amino acids, which is substantially free of cellular material or culture medium when produced by recombinant DNA techniques, or chemical precursors or other chemicals when chemically synthesized. The link between one amino acid residue and the next is an amide bond, and is sometimes referred to as a peptide bond. In this invention, the amino acid sequence as set forth in SEQ ID NO: 3 can be produced by introducing the polynucleotide sequence having a substantial amount of sequence identity to SEQ ID NO: 1 or SEQ ID NO: 2 into prokaryotic such as E. coli or eukaryotic host cells such as hepatocytes, Chinese hamster ovary cells or 293 cells, or yeast such as S. Cerevisiae with the aid of a recombinant vector or construct, operably linked to a promoter such as terminal protein (TP), T7, T3 or Sp6, using experiment procedures known to the person skilled in the arts such as transfection, transformation or electroporation, to produce the amino acid sequence. In addition to use an expression system mentioned above to prepare polypeptide sequence, analogous polypeptide sequence as set forth in SEQ ID NO: 3 can be prepared synthetically by placing the polynucleotide sequence having a substantial amount of sequence identity to SEQ ID NO: 1 or SEQ ID NO: 2 directly under the control of specific promoter such as terminal protein (TP), T7, T3 or Sp6 promoters to generate the claimed peptide by in vitro transcription coupled with in vitro translation system. The polypeptide can also be prepared directly by isolation and purification from various HBV genotypes.

Again a series of experiments were conducted, including sequence alignment and molecular modeling, plasmid constructs, point mutation and other experiments such as cell culture and transfection, Isolation of intracellular replicative intermediates from transfected cells, Southern blotting, Northern blotting, HBV pgRNA packaging assay, Endogenous polymerase reaction (EPR), and Assay for inhibitory activity against HBV replication according to Examples 1 through 9, to monitor the replication efficiencies and encapsidation efficiencies of the helix-turn-helix mutants.

The experimental results revealed that the regulation of HBV replication is still effective if the isolated amino acid sequence varies substantial amount, which is at least 50% of the amino acid sequence identity as set forth in SEQ ID NO: 3. The term "percent (%) identity" as used in the context of amino acid sequence (e.g., when one amino acid sequence is said to be X % identical to another amino acid sequence) refers to the percentage of identical residues shared between the two sequences, when optimally aligned. To determine the percent identity of two amino acid sequences, the sequences are aligned for optimal comparison purposes (e.g. gaps may be introduced in one sequence for optimal alignment with the other sequence). The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences. Based on the fact of the above mentioned function of amino acid sequence of the helix-turn-helix of the helix clamp of HBV RT, new drugs and biological substances can be designed and screened to act on the sequence, or interact with the sequence to interfere the replication of HBV replication. The new drugs and biological substances can be a recombinantly-produced amino acid sequence comprising a substantial amount of sequence identity to the SEQ ID NO: 3, or a chemically-synthesized amino acid sequence comprising a substantial amount of sequence identity to SEQ ID NO: 3. The polypeptide with a drug is administered to a patient. The polypeptide inhibits HBV pgRNA encapsidation, thereby stopping the HBV replication process.

One embodiment provides a method for screening inhibitors to bind the amino acid sequence of the helix-turn-helix (helix clamp) of HBV RT, base on the experiment samples, comprises the steps of: 1) providing an amino acid sequence as an anti-HBV target having a substantial amount of sequence identity to SEQ ID NO: 3, 2) providing a candidate substance from a population of substances, 3) introducing the candidate substance to react with the amino acid sequence, and 4) detecting the effect of inhibition of HBV replication. The candidate substances are antibodies, chemical compounds, polynucleotides, and herb medicines.

The method for screening inhibitors to bind the amino acid sequence having a substantial amount of sequence identity to SEQ ID NO: 3 comprises building a candidate substance library from a population of substances, such as antibodies, chemical compounds, polynucleotides, and herb medicines, by predicting potential candidates by ligand orientation evaluation based on DOCK algorithm, steric complementarity, chemical complementarity, using the intermolecular van der Waals force, or the intermolecular electrostaticterms from the AMBER force-field. The library may also include the molecules from the database for anti HBV agent screening, in which a polynucleotide sequence as set forth in SEQ ID NO: 1 or SEQ ID NO: 2 is the target as descried previously.

The method for screening inhibitors to bind the amino acid sequence having a substantial amount of sequence identity to SEQ ID NO: 3, further evaluates the library of candidates for their solubility, toxicity, ease of analog synthesis, and the effect of inhibition of HBV replication. The inhibitory effects to HBV replication of the candidates are tested by reacting potential candidate substances with the amino acid sequence of the helix-turn-helix (helix clamp) of HBV RT in assays, in animal models, and with patients clinically for their inhibitory activity against HBV replication. In addition, toxilogical data of potential candidate substances are collected using animal models.

The polypeptide or the amino acid sequence of the helix-turn-helix (helix clamp) of HBV RT according to this invention is expected to be immunogenic, in other words, it is able to induce an antibody response in a mammalian organism. These specific antibodies targeting the helix-turn-helix (helix clamp) would also interfere with HBV polymerase functions to inhibit HBV replication.

Since helix-turn-helix (helix clamp) plays crucial roles in HBV replication by maintaining the active configuration of HBV polymerase, the antibodies targeting the helix-turn-helix epitope will interfere with the configuration of HBV polymerase. Therefore, the helix-turn-helix (helix clamp) of HBV RT can be used as a new anti-HBV target for anti-HBV agent design.

Currently, immunology technique and commercial services (Phoenix Biotech Co., Ltd, Beijing, China and ABGENT, San Diego, USA) to prepare antibodies to a short peptide are available to design and manufacture the required antibodies. The procedure of preparing monoclonal antibody to HBV polymerase inhibiting polymerase activity can also be found from J. Virol. 1999, 73: 4188-4196, which is hereby incorporated as a reference.

The procedures used in the experiments were: Sequence alignment and molecular modeling, Plasmid constructs, Cell culture and transfection, Isolation of intracellular replicative intermediates from transfected cells, Southern blotting, Northern blotting, HBV pgRNA packaging assay, Endogenous polymerase reaction (EPR), Assay for inhibitory activity against HBV replication, and PCR.

The experiment procedures to isolate the nucleotide sequence coding for amino acid sequences, to amplify the nucleotide sequence such as PCR, to introduce vectors or constructs operably linked to a promoter such as terminal protein (TP), T7, T3 or Sp6, into appropriate host cells such as transfection and transduction were also used in the experiments.

The methods known to the person skilled in the art were used in the experiments. The skilled person is familiar with the fact that, after the isolation of the nucleotide sequence coding for the claimed peptide using methods according to the prior art such as PCR, the polynucleotide sequence operably linked to a promoter such as terminal protein (TP), T7, T3 or Sp6, can be either introduced into prokaryotic such as *E. coli* or eukaryotic host cells such as hepatocyte, Chinese hamster ovary cell or 293 cell, or yeast such as *S. Cerevisiae* with the aid of a recombinant vector or construct, using methods such as transfection, transformation or electroporation, to produce the claimed polypeptide, or placed the nucleotide sequence directly under the control of specific promoter such as terminal protein (TP), T7, T3 or Sp6 promoters to generate the claimed peptide by in vitro transcription coupled with in vitro translation system. In addition to use an expression system mentioned above to prepare polypeptides, analogous polypeptide can be also prepared synthetically or prepared directly by isolation and purification from various HBV genotypes.

Other experiment procedures well known to persons skilled in the art, can be found in transfection, transformation or electroporation: Molecular Cloning: A Laboratory Manual, 2nd ed., Vol. 1-3, Sambrook et al., Cold Spring Harbor Laboratory Press (1989), which is hereby incorporated as reference.

The invention will be further described in the following examples, which do not limit the scope of the invention described in the claims.

EXAMPLE 1

Sequence Alignment and Molecular Modeling

GenBank accession numbers of the reference eight genotype (A to H) HBV strains are as follows: A-X02763, Aafr-AF297621, Ba-D00330, Bj-AB073858, C-AB033556, Caus-AB048704, D-X02496, E-X75657, F-X69798, G-AF160501 and H-AY090454. The thumb subdomains (RT 266 to RT 351) of representative A to H genotype HBV strains were used for alignment using program CLUSTAL-W. As described previously (Nucleic Acids Res, 1994, 22:4625-4633.), all protein sequences or secondary structures used for helix clamp alignments were derived from Swiss-Prot sequence database, NCBI protein database or the Protein Data Bank (PDB). Three-dimensional structure modeling of HBV RT was performed as described previously (J. Virol., 2001, 75:11827-11833.).

EXAMPLE 2

Plasmid Constructs

An HBV replicon plasmid harboring 1.3 copies of HBV genome was constructed following the standard methods. In brief, 3.2 kb of full-length HBV genome fragments cleaved from plasmids pUC-HBV#97 (Genotype C, GenBank accession number: AF411411) by Sapi (New England Biolab) were self-ligated with T4 DNA ligase (New England Biolab). Using ligation products as templates, two fragments (A and B) were respectively amplified with the following primers: A: 5'-AAACTGCAGCTGCCTGTAAATAGACCTATTG-3'/5'-GCTGTAGCTCTTGTTCCCAAG-3'; B: 5'-CTCAGTC-CGTTTCTCCTGGC-3'/5'-CGGGGTACCGAGAGT AACTCCACAGAAGCTC-3' (Sequences underlined denote recognition sites of PstI and KpnI respectively). A was digested by PstI and BstEII (New England Biolab), while B was cut with SpeI and KpnI (New England Biolab). HBV replicon plasmid was completed through a two-step cloning strategy: digested A was firstly cloned into pUC-HBV97 between PstI and BstEII restriction sites, subsequently digested B was inserted into the SpeI-KpnI sites of the recombinant plasmid pUC-HBV97-A. This recombinant plasmid is replicative competent.

Based on the constructed HBV replicon plasmid, site-directed mutants (FIGS. 4 and 5) introducing the following mutations (RTP306G, P306A, P306S, P306V, P306D, P306L, P306E, P306K, P306F, G304A, G304F, Y305A, A307F, L308A, L308F and L311A) were developed by overlapping PCR described previously. Two mutants (RTL336A and RTS346A) with residues outside of the helix clamp were also constructed, and RTW58*, a polymerase depleted replicon which has a stop codon at residue 58 in the RT domain, was also constructed.

For construction of eukaryotic expression plasmid for HBV core protein, 550-bp core coding sequence was amplified from pUC-HBV#97 with the primers: 5'-GTCTAGCTAGCGCCACCATGGACATTGA-CACCTATAAAG-3'/5'-CGGGGTACCCTAACAT-TGAGATTCCCGAGAT-3' (Sequences underlined denote recognition sites of NheI and KpnI respectively) and cloned into the NheI and KpnI sites of pcDNA3.1/Hygro(−) (Invitrogen) to obtain pcDNA-core.

To generate the template for HBV specific antisense riboprobe, 460-bp HBV X protein (HBx) coding sequence was amplified by the following primers: 5'-CGGGGTACCTTAG-GCAGAGGTGAAAAAGTTG-3'/5'-GCTCTAGAATG-GCTGCTAGGATGTGCTG-3' (sequence underlined represented recognition site of KpnI and XbaI) and cloned into pBluescript SK (+) (Stratagene) to construct pBlue-X. For in vitro transcription, pBlue-X was firstly linearized with XbaI (New England Biolab), and was recovered and dissolved in DEPC water.

EXAMPLE 3

Cell Culture and Transfection

Huh-7 cells (hepatocarcinoma cell line) or HepG2.2.15 cells or HepAD38 cells were cultured in DMEM (Invitrogen) supplemented with 10% fetal bovine serum, 100 U/ml penicillin G and 100 mg/ml streptomycin, 0.2 mM L-glutamine, at 5% CO2. Ten mg of recombinant wild type or mutant HBV DNA and 5 mg pEGFP-C2 encoding a green fluorescent protein (Clontech) or pSEAP2-Control expressing secreted alkaline phosphatase (SEAP) were co-transfected to Huh-7 cells to monitor the transfection efficiency by the calcium phosphate co-precipitation method (J. Virol., 2001, 75:11827-11833.).

EXAMPLE 4

Isolation of Intracellular Replicative Intermediates from Transfected Cells Cells were lysed with lysis solution (10 mM Tris-HCl, pH 7.9, 1 mM EDTA, 100 mM NaCl and 1% NP-40) and incubated with DNase I, RNaseA and magnesium acetate to remove free nucleic acids. After centrifugation, intracellular viral capsids were precipitated with 6.5% PEG8,000 and 0.3M NaCl, and disrupted with proteinase K overnight. HBV DNA was extracted twice with phenol:chloroform (1:1), precipitated with ethanol and sodium acetate, and dissolved in distilled deionized water.

EXAMPLE 5

Southern Blotting

As reported, HBV capsid DNA fractionated on 1% TAE agarose gels was transferred onto nylon membranes and hybridized at 42° C. with HBV specific 32P-labeled probes prepared by random primer labeling (Roche diagnostics). The membranes were washed as the following procedure: 2×SSC, 0.5% SDS at room temperature for 5 min; 2×SSC, 0.1% SDS at room temperature for 15 min; 0.1×SSC, 0.1% SDS at 65 degree C. for 60 min; 0.1×SSC at room temperature for 10 min and exposed to phosphorimage plates, and scanned by a phosphorimage reader (Fujifilm). Densitometry of each lane was performed using MultiGauge V2.2 software (Fujifilm). Replication efficiencies of mutants are represented as the amount of intracellular viral replicative intermediates of mutants normalized to that of capsids detected by Western blotting.

EXAMPLE 6

Northern Blotting

Total cellular RNA was extracted from transfected cells with Trizol reagent (Invitrogen). Following the standard method (Molecular Cloning: A Laboratory Manual, 2nd ed., Vol. 1-3, Sambrook et al., Cold Spring Harbor Laboratory Press (1989)), 20 micrograms of RNA was separated on agarose/formaldehyde gels, transferred onto nylon membranes, and fixed on membranes by UV irradiation. Hybridization and exposure were similar to that described in Southern blotting.

EXAMPLE 7

HBV pgRNA Packaging Assay

HBV pgRNA packaging efficiency was determined as previously reported (J. Virol., 1994, 68: 4341-4348.) with some modifications. In brief, for immunodetection of core particles, cleared lysate was electrophoresed on a native agarose gel and transferred onto a nitrocellulose membrane. The amount of assembled core particles was probed sequentially by polyclonal anti-HBcAg (Dako), HRP-labeled anti-rabbit secondary antibody (Amersham Pharmacia Biotech) and chemiluminescence reagents (Pierce). For detection of packaged pgRNA, nucleic acids in the capsids were in situ released with treatment of 0.2 M NaOH/1.5 M NaCl for 30 seconds followed by neutralization in 0.2 M Tris-HCl, pH 7.4/1.5 M NaCl for 5 min and probed with a 32P-labeled antisense HBV riboprobe targeting the HBx coding region of pgRNA, which was produced by in vitro transcription following the manual (Promega). The packaging efficiency was calculated as signal intensity of encapsidated pgRNA normalized to that of the corresponding capsids.

EXAMPLE 8

Endogenous Polymerase Reaction (EPR)

As reported by Radziwill et al (Radziwill et al., 1990), transfected cells were lysed and intracellular core particles were immunoprecipitated with protein A sepharose CL-4B beads coated with polyclonal anti-HBcAg. After washing, reaction buffer with 50 mM Tris-HCl, pH 7.5, 75 mM NH4Cl, 1 mM EDTA, 20 mM MgCl2, 0.1% (vol/vol) β-mercaptoethanol, 0.5% (vol/vol) Nonidet P-40, 0.4 mM dATP, 0.4 mM dGTP, 0.4 mM dTTP and 10 µCi [α-32P]dCTP (3,000 Ci/mmol) was added to the beads. Following incubation, labeled capsid DNA was released with proteinase K treatment, recovered and separated on a 1% TAE agarose gel, transferred onto a Nylon membrane. The membrane was exposed to a phosphorimage plate and scanned by a phosphorimage reader (Fujifilm). Transfection efficiency was normalized with SEAP activity analyzed as mentioned above.

EXAMPLE 9

Assay for Inhibitory Activity Against HBV Replication

Stable HBV producing cells (e.g. HepG2.2.15 cells or HepAD38 cells) are seeded at a density of 1×10 cells per well in 24-well plate and cultured to be confluent. The cells are refeed with fresh DMEM in the presence of increasing concentrations of potential anti-HBV agents. The media will be refreshed every two day with DMEM containing potential anti-HBV agents. At the day 9, the cells are washed with PBS twice and lysed with TNE buffer (10 mM Tris-HCl, pH 7.9, 1 mM EDTA, 100 mM NaCl) supplemented with 1% NP40. After centrifugation at 12,000 g for 2 min, the supernatants are incubated with DNase I, RNaseA and magnesium acetate to remove free nucleic acids. After centrifugation, intracellular viral capsids are precipitated with 6.5% PEG8,000 and 0.3 M NaCl, and disrupted with proteinase K overnight. HBV DNA is extracted twice with phenol:chloroform (1:1), precipitated with ethanol and sodium acetate, and dissolved in distilled deionized water. Subsequently HBV capsid DNA fractionated on 1% TAE agarose gels is transferred onto nylon membranes and hybridized at 42 degree C. with HBV specific 32P-labeled probes prepared by random primer labeling (Roche diagnostics). The membranes are washed as the following procedure: 2×SSC, 0.5% SDS at room temperature for 5 min; 2×SSC, 0.1% SDS at room temperature for 15 min; 0.1×SSC, 0.1% SDS at 65 degree C. for 60 min; 0.1×SSC at room temperature for 10 min and exposed to phosphorimage plates, and scanned by a phosphorimage reader (Fujifilm). Densitometry of each lane is performed using MultiGauge V2.2 software (Fujifilm). The effects of potential anti-HBV agent on HBV replication will be obtained by comparing the amount of intracellular replicative intermediates from treatment groups to that of no-treatment groups.

In the foregoing description and examples, limited and narrow interpretation of descriptive language intended to better illustrate the invention is not to be construed as limiting in any way nor to limit the scope of the invention contemplated by the inventor. It will be clear that the invention may be practiced otherwise than as particularly described in the foregoing description and examples. Numerous modifications and variations of the present invention are possible in light of the above teachings and, therefore, are within the scope of the appended claims.

What is claimed is:

1. A method to screen for anti-HBV agents which are inhibitors to HBV replication, comprising: evaluating a substance for ability to bind to an amino acid sequence with at least 50% identity to SEQ ID NO: 3 in a helix-turn-helix structure, using molecular modeling or reaction of the substance with the amino acid sequence, and, if the substance is evaluated as able to bind, testing the substance for inhibitory effects on HBV replication.

2. The method to screen for anti-HBV agents of claim 1, wherein the substance is a chemical compound.

3. The method to screen for anti-HBV agents of claim 1, wherein the substance is selected from a library of candidate substances.

4. The method to screen for anti-HBV agents of claim 3, wherein the library comprises potential candidates predicted by ligand orientation evaluation based on DOCK algorithm.

5. The method to screen for anti-HBV agents of claim 3, wherein the library comprises potential candidates predicted by ligand orientation evaluation based on steric complementarity.

6. The method to screen for anti-HBV agents of claim 3, wherein the library comprises potential candidates predicted by ligand orientation evaluation based on chemical complementarity.

7. The method to screen for anti-HBV agents of claim 1, wherein the ability to bind to said amino acid sequence is measured by intermolecular van der Waals force from the AMBER force-field.

8. The method to screen for anti-HBV agents of claim 1, wherein the ability to bind to said amino acid sequence is measured by intermolecular electrostaticterms from the AMBER force-field.

9. The method to screen for anti-HBV agents of claim 3, wherein the library comprises potential candidates predicted by ligand binding to pockets surrounding the helix-turn-helix of helix clamp at the base of the thumb subdomain of the RT domain of HBV polymerase.

10. The method to screen for anti-HBV agents of claim 3, wherein the library comprises potential candidates selected from Phenylalanine derivatives.

11. The method to screen for anti-HBV agents of claim 1, wherein the inhibitory effect on HBV replication is determined by measuring the amount of HBV DNA in HBV producing stable cells.

12. The method to screen for anti-HBV agents of claim 1, further comprising a step of biological testing of the inhibitor on an animal model to further select an effective inhibitor to HBV replication.

13. The method to screen for anti-HBV agents of claim 1, further comprising a step of toxicology testing of the inhibitor on an animal model.

14. The method to screen for anti-HBV agents of claim 1, further comprising a step of clinical testing of the inhibitor on a patient to further select an effective inhibitor to HBV replication.

* * * * *

SEQUENCE LISTING

```
<160> NUMBER OF SEQ ID NOS: 13

<210> SEQ ID NO 1
<211> LENGTH: 36
<212> TYPE: DNA
<213> ORGANISM: Hepatitis B virus
<220> FEATURE:
<221> NAME/KEY: exon
<222> LOCATION: (1)..(36)

<400> SEQUENCE: 1 ttt aca caa tgt ggc tat cct gct tta atg cct tta                         36
Phe Thr Gln Cys Gly Tyr Pro Ala Leu Met Pro Leu
1               5                   10

<210> SEQ ID NO 2
<211> LENGTH: 36
<212> TYPE: DNA
<213> ORGANISM: Hepatitis B virus
<220> FEATURE:
<221> NAME/KEY: exon
<222> LOCATION: (1)..(36)

<400> SEQUENCE: 2 taa agg cat taa agc agg ata gcc aca ttg tgt aaa                         36
    Arg His     Ser Arg Ile Ala Thr Leu Cys Lys
    1               5                   10

<210> SEQ ID NO 3
<211> LENGTH: 12
<212> TYPE: PRT
<213> ORGANISM: Hepatitis B virus
<220> FEATURE:
<221> NAME/KEY: MISC_FEATURE
<222> LOCATION: (1)..(12)
```

-continued

<400> SEQUENCE: 3

Phe Thr Gln Cys Gly Tyr Pro Ala Leu Met Pro Leu
1               5                   10

<210> SEQ ID NO 4
<211> LENGTH: 86
<212> TYPE: PRT
<213> ORGANISM: Hepatitis B virus
<220> FEATURE:
<221> NAME/KEY: PEPTIDE
<222> LOCATION: (1)..(86)

<400> SEQUENCE: 4

Val Leu Lys Ile Lys Gln Cys Phe Arg Lys Leu Pro Val Asn Arg Pro
1               5                   10                  15

Ile Asp Trp Lys Val Cys Gln Arg Ile Val Gly Leu Leu Gly Phe Ala
                20                  25                  30

Ala Pro Phe Thr Gln Cys Gly Tyr Pro Ala Leu Met Pro Leu Tyr Ala
            35                  40                  45

Cys Ile Gln Ser Lys Gln Ala Phe Thr Phe Ser Pro Thr Tyr Lys Ala
        50                  55                  60

Phe Leu Cys Lys Gln Tyr Leu Asn Leu Tyr Pro Val Ala Arg Gln Arg
65                  70                  75                  80

Ser Gly Leu Cys Gln Val
                85

<210> SEQ ID NO 5
<211> LENGTH: 32
<212> TYPE: PRT
<213> ORGANISM: Hepatitis B virus
<220> FEATURE:
<221> NAME/KEY: HELIX
<222> LOCATION: (1)..(32)

<400> SEQUENCE: 5

Gln Arg Ile Val Gly Leu Leu Gly Phe Ala Ala Pro Phe Thr Gln Cys
1               5                   10                  15

Gly Tyr Pro Ala Leu Met Pro Leu Tyr Ala Cys Ile Gln Ala Lys Gln
                20                  25                  30

<210> SEQ ID NO 6
<211> LENGTH: 32
<212> TYPE: PRT
<213> ORGANISM: Hepatitis C virus
<220> FEATURE:
<221> NAME/KEY: HELIX
<222> LOCATION: (1)..(32)

<400> SEQUENCE: 6

Thr Ala Arg His Thr Pro Val Asn Ser Trp Leu Gly Asn Ile Ile Met
1               5                   10                  15

Tyr Ala Pro Thr Leu Trp Ala Arg Met Ile Leu Met Thr His Phe Phe
                20                  25                  30

<210> SEQ ID NO 7
<211> LENGTH: 32
<212> TYPE: PRT
<213> ORGANISM: Human immunodeficiency virus type 1
<220> FEATURE:
<221> NAME/KEY: HELIX
<222> LOCATION: (1)..(32)

```
<400> SEQUENCE: 7

Val Asn Asp Ile Gln Lys Leu Val Gly Lys Leu Asn Trp Ala Ser Gln
1               5                   10                  15

Ile Tyr Pro Gly Ile Lys Val Arg Gln Leu Ser Lys Leu Leu Arg Gly
            20                  25                  30

<210> SEQ ID NO 8
<211> LENGTH: 32
<212> TYPE: PRT
<213> ORGANISM: Human immunodeficiency virus type 2
<220> FEATURE:
<221> NAME/KEY: HELIX
<222> LOCATION: (1)..(32)

<400> SEQUENCE: 8

Val Asn Ala Ile Gln Lys Leu Val Gly Val Leu Asn Trp Ala Ala Gln
1               5                   10                  15

Leu Phe Pro Gly Ile Lys Thr Arg His Ile Cys Lys Leu Ile Arg Gly
            20                  25                  30

<210> SEQ ID NO 9
<211> LENGTH: 32
<212> TYPE: PRT
<213> ORGANISM: Simian immunodeficiency virus
<220> FEATURE:
<221> NAME/KEY: HELIX
<222> LOCATION: (1)..(32)

<400> SEQUENCE: 9

Val Asn Asp Leu Gln Lys Leu Val Gly Lys Leu Asn Trp Ala Ala Gln
1               5                   10                  15

Leu Tyr Pro Gly Leu Arg Thr Lys Asn Ile Cys Lys Leu Leu Arg Gly
            20                  25                  30

<210> SEQ ID NO 10
<211> LENGTH: 32
<212> TYPE: PRT
<213> ORGANISM: Canine influenza virus
<220> FEATURE:
<221> NAME/KEY: HELIX
<222> LOCATION: (1)..(32)

<400> SEQUENCE: 10

Val Asn Asp Ile Gln Lys Leu Ile Gly Lys Leu Asn Trp Ala Ser Gln
1               5                   10                  15

Ile Tyr Pro Gly Ile Lys Ile Lys Gln Leu Cys Lys Leu Ile Arg Gly
            20                  25                  30

<210> SEQ ID NO 11
<211> LENGTH: 32
<212> TYPE: PRT
<213> ORGANISM: SARS coronavirus
<220> FEATURE:
<221> NAME/KEY: HELIX
<222> LOCATION: (1)..(32)

<400> SEQUENCE: 11

Thr Asp Gly Thr Leu Met Ile Glu Arg Phe Val Ser Leu Ala Ile Asp
1               5                   10                  15

Ala Tyr Pro Leu Thr Lys His Pro Asn Gln Glu Tyr Ala Asp Val Phe
            20                  25                  30
```

```
<210> SEQ ID NO 12
<211> LENGTH: 32
<212> TYPE: PRT
<213> ORGANISM: Varicella zoster virus
<220> FEATURE:
<221> NAME/KEY: HELIX
<222> LOCATION: (1)..(32)

<400> SEQUENCE: 12

Glu Lys Cys Ile Gln Asp Ser Ala Leu Val Gly Lys Leu Phe Phe Lys
1               5                   10                  15

Arg Leu Pro His Leu Glu Leu Ser Ala Val Ala Lys Leu Lys Arg Ile
            20                  25                  30

<210> SEQ ID NO 13
<211> LENGTH: 32
<212> TYPE: PRT
<213> ORGANISM: Equine Herpes Virus -1
<220> FEATURE:
<221> NAME/KEY: HELIX
<222> LOCATION: (1)..(32)

<400> SEQUENCE: 13

Glu Tyr Cys Ile Gln Asp Ser Arg Leu Val Gly Lys Leu Phe Phe Lys
1               5                   10                  15

Tyr Leu Pro His Leu Glu Leu Ser Ala Val Ala Lys Leu Ala Arg Ile
            20                  25                  30
```